United States Patent [19]

Miller

[11] Patent Number: 5,072,725
[45] Date of Patent: Dec. 17, 1991

[54] SOFT BODY BRACE

[76] Inventor: Marion E. Miller, Seaquay Condominiums, 4800 N. A-1-A, Unit 418, Vero Beach, Fla. 32963

[21] Appl. No.: 515,507

[22] Filed: Apr. 27, 1990

[51] Int. Cl.$^5$ .............................................. A61F 5/02
[52] U.S. Cl. ...................................... 128/78; 128/85; 128/87 R; 128/869
[58] Field of Search ............... 128/78, 89 R, 90, 87 R, 128/869, 874, 95.1, 96.1, 80 R, 83, 85, 99.1, 870, 878, 882; 2/44, 92

[56] References Cited

U.S. PATENT DOCUMENTS

| 2,655,916 | 10/1953 | Timmins | 128/87 R |
| 3,717,143 | 2/1973 | Johnson | 128/78 |
| 3,871,367 | 3/1975 | Miller | 128/78 |
| 4,022,197 | 5/1977 | Castiglia | 128/78 X |
| 4,688,558 | 8/1987 | Hooper et al. | 128/78 |

FOREIGN PATENT DOCUMENTS 0099783 2/1984 European Pat. Off. .............. 128/78

OTHER PUBLICATIONS

Freeman Back Supports Ad, Journal of Bone & Joint Surgery, p. 53, Jul. 1955.
Zimmer Ad, Journal of Bone & Joint Surgery, British vol. 50-B, No. 2, May 1968.

Primary Examiner—Robert Bahr
Assistant Examiner—J. Doyle
Attorney, Agent, or Firm—Irving M. Kriegsman; Edward M. Kriegsman

[57] ABSTRACT

A soft body brace for providing support for certain types of patients includes an inner layer of soft compressible plastic material and an outer layer of soft compressible plastic material, the outer layer of soft compressible plastic material being bonded to the inner layer of soft compressible plastic material and along with the inner layer defining a shell configured to circumscribe the torso of the wearer and having a split portion. A plurality of sleeves of flexible material are sandwiched between the inner and outer layers and a reinforcing stay is fixedly disposed in each sleeve for maintaining the brace in its intended shape. Releasable fasteners are attached to the split portion for maintaining the brace in place on the wearer. In making the soft body brace the shell is first fabricated and then shaped as necessary to conform to the shape of the intended wearer. Reinforcing stays are then cut to size bent as needed to conform to the shape of the wearer at their intended locations and inserted into their respective sleeves. The ends of the sleeves are then sealed off to prevent removal of the reinforcing stays. The fastener assemblies are then attached to the split portion of the shell.

13 Claims, 5 Drawing Sheets

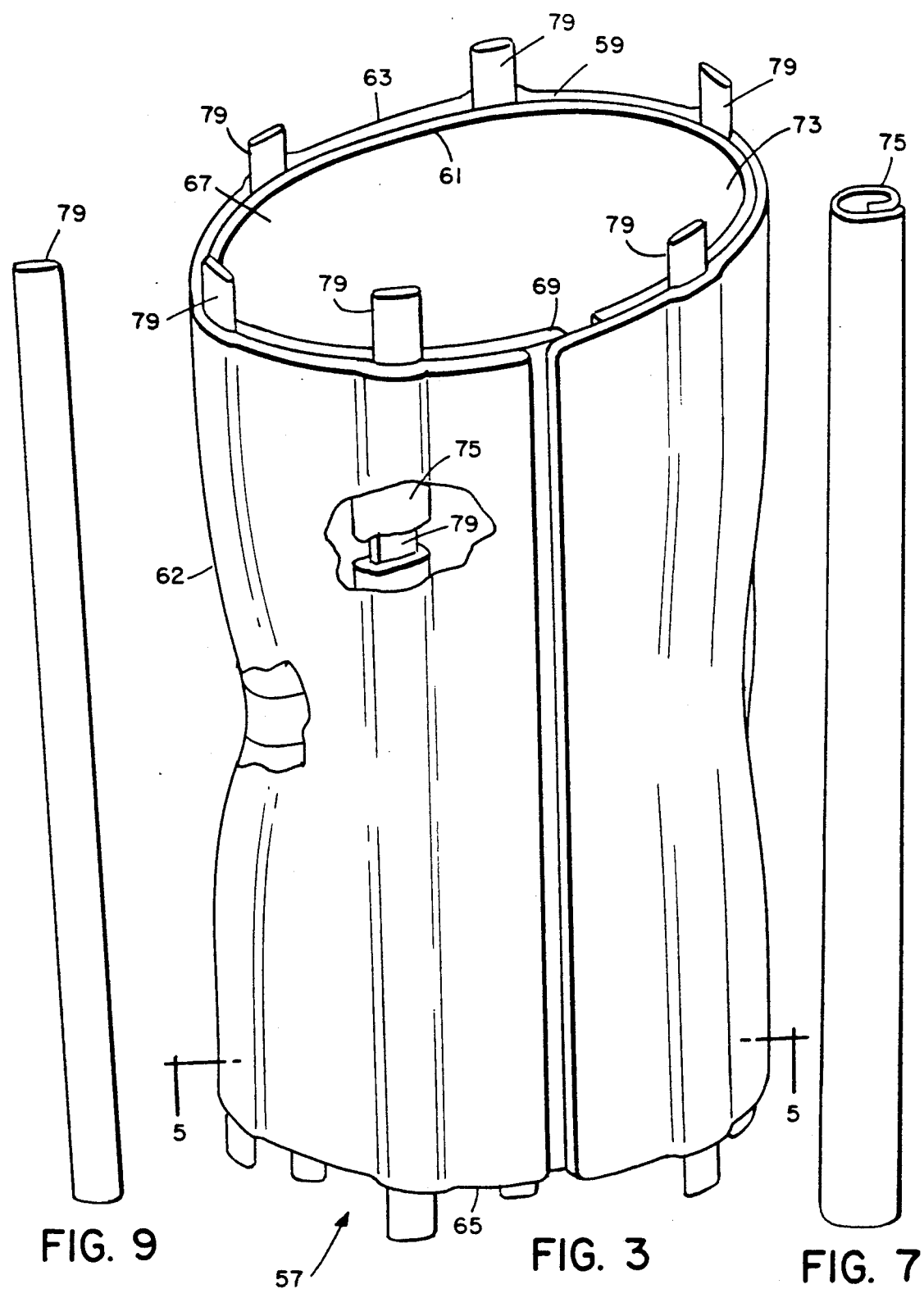

SOFT BODY BRACE

BACKGROUND OF THE INVENTION

The present invention relates generally to a body brace and, more particularly, to a soft body brace.

Body braces are well known in the art and have been used in the past for correcting various abnormalities or deformaties of the spine and/or for providing support.

In U.S. Pat. No. 3,871,367 to M. E. Miller there is disclosed a body brace which is constructed to be used for corrective purposes. The brace comprises an outer layer of a hard substantially rigid plastic material and an inner layer of soft compressible plastic material, with the inner layer being bonded to the outer layer. The brace is shaped to engage a person's pelvis and includes an anterior portion, a vertically split posterior portion, releasable fastening means secured to the adjacent posterior portions to aid in securing the brace to a wearer, and inwardly curved sections in both layers of the brace for engaging the iliac crests of the wearer, the inwardly curved sections having appreciably thicker compressible inner layers thereon. The brace has become known in the field as the Boston Body Brace.

Another known type of body brace constructed to be used for corrective purposes comprises a shell which is sized and configured so as to circumscribe the trunk of the body and having a vertical length so as to extend at the posterior side from approximately the sacrum to approximately the eighth dorsal and at the anterior side from approximately the pubic region to approximately the upper limit of the diaphram, the shell being comprised of a flexible sheet of hard substantially rigid plastic material structured to provide a girdle having a continuous posterior side, overlapping anterior sides and lateral sides, the lateral sides containing indentations commencing at the posterior side extending forwardly therefrom and terminating at the anterior side and embodying laterally divergent portions above and below the indentations dimensioned to receive, respectively, the lower part of the rib cage and the upper part of the pelvis, transversely-spaced, vertically disposed parallel stays fixed to the girdle at substantially equal distances from the ends of the overlapping anterior sides and cinches connected to the respective stays adjustable to constrain the girdle about the body. The device is referred to in the field as the Boston Overlap Brace.

Both of the above described braces are classified as hard body braces in that they contain at least one layer of a hard substantially rigid material.

In my copending U.S. patent application Ser. No. 508,199 filed on Apr. 11, 1990 there is disclosed a body brace which is constructed to be used for providing support for certain types of patients. The brace is intended to be used, for example, by the muscular dystrophy patient whose progressive muscular atrophy leaves little strength for breathing and little tissue to cover bony areas, or by the severe scoliotic patient whose breathing is already compromised by a malaligned anatomy and support is indicated to relieve internal pressures, or by the insensate patient, such as the myelomeningocele, where unfelt pressure is a risk or by the cerebral palsy patient whose involuntary spasticity can be of great discomfort within a completely rigid brace.

Briefly, the body brace described in the above noted pending application serial number comprises a shell having an outer layer of a soft compressible plastic material and an inner layer of soft compressible plastic material, with the inner layer being bonded to the outer layer. The brace is shaped to circumscribe the person's torso and includes posterior and anterior portions, one of the two portions being vertically split. Releasable fasteners are secured to the split portion to aid in securing the brace on the wearer. Inwardly curved pads are fixedly sandwiched between the two layers of soft compressible plastic material for engaging the iliac crests of the wearer. The brace further includes a plurality of reinforcing stays for maintaining the brace in its intended shape. The reinforcing stays are made of plastic and are fixedly sandwiched between the two layers of soft compressible plastic material, are transversely spaced from each other and are vertically oriented.

The body brace described in the above noted pending patent application is a soft type of body brace in that the inner and outer layers making up the shell are both made of soft compressible material.

The body brace in the above noted pending patent application may be fabricated in the following manner. Using measurements of the patient taken by an orthotist or a cast corresponding to the shape of the patient which may be made by the orthotist, the manufacturer selects from a group of molds on hand a mold that most nearly approximates the size and shape of the patient. The manufacturer then adds plaster to the mold where needed so as to make the mold conform as closely as possible to the exact shape of the patient. The brace is then formed on the modified mold by first pulling the inner layer, then attaching the crest pads and reinforcing stays to the inner layer, bending the stays where necessary to conform to the shape of the modified mold, then forming the outer layer, over the inner layer, crest pads and stays and then attaching the releasable fasteners. The brace is then trimmed by the orthotist, as needed, to conform to the size of the wearer.

One of the problems with the above described body brace as so manufactured and then assembled is that the orthotist can trim the brace received from the manufacturer to conform to the size of the wearer but cannot make any fine adjustments in the shape of the brace if such adjustments are needed in order to conform more closely to the exact shape of the wearer. More specifically, once the brace has been fabricated the two layers of soft compressible material cannot be reshaped and the reinforcing stays cannot be bent additionally or to a lesser degree, in order to conform more closely to the shape of the wearer. Another problem with the above described soft body brace as so fabricated is that it is time consuming for the orthotist to take measurements or make a cast, send the measurements or the cast to the manufacturer who is usually not close by, wait for the brace to be made and shipped to him and then trim the brace to accommodate the wearer.

As can be appreciated, it would be very beneficial if the orthotist could have a body brace which could be customized on site to the particular shape as well as the size of the wearer.

Accordingly, it is an object of this invention to provide a new and improved body brace.

It is a further object of this invention to provide a new and improved soft body brace.

It is another object of this invention to provide a new and improved method of making a soft body brace.

It is still another object of this invention to provide an unfinished soft body brace which can be easily finished to provide a soft body brace customized to the size and shape of the intended wearer.

It is yet still another object of this invention to provide a method of making an unfinished soft body brace which can then be finished to make a soft body brace customized to the size and shape of the intended wearer.

It is a further object of this invention to provide an unfinished soft body brace which can be customized on site to make a finished soft body brace.

It is still a further object of this invention to provide a soft body brace which can be customized to meet the specific shape of the intended wearer without having to first take extensive measurements and without having to first make a cast of the wearer.

It is yet still a further object of this invention to provide a soft body brace which is easy to manufacture and effective when being worn.

SUMMARY OF THE INVENTION

A soft body brace constructed according to the teachings of the present invention comprises an inner layer of soft compressible plastic material, an outer layer of soft compressible plastic material, the outer layer of soft compressible plastic material being bonded to the inner layer of soft compressible plastic material, the inner and outer layers defining a shell configured to circumscribe the torso of the wearer and having a split portion, a plurality of elongated sleeves of flexible material fixedly sandwiched between the inner an outer layers of soft compressible plastic material, a reinforcing stay disposed in each sleeve for maintaining the shell in a desired shape, and releasable fasteners attached to the split portion of the shell for maintaining the brace in place on the wearer.

The soft body brace of the present invention may be fabricated in the following manner.

First, an unfinished soft body brace is fabricated, the unfinished soft body brace comprising an inner layer of soft compressible plastic material, an outer layer of soft compressible plastic material bonded to the inner layer of soft compressible plastic material, the inner and outer layers defining a substantially cylindrical sheet having a split portion, a plurality of sleeves fixedly sandwiched between the inner and outer layers and a reinforcing stay removably mounted in each sleeve. Then, the reinforcing stays are removed from the shell. Then the shell is shaped where needed to conform to the specific shape of the intended wearer. Then, the reinforcing stays are bent to conform to the shape of the wearer at their intended locations on the shell and inserted back into their respective sleeves. Then, the sleeves are sealed off at each end to prevent removal of the reinforcing stays. Then, the releasable fasteners are attached to the split portion of the shell.

As can be appreciated, the unfinished soft body brace can be fabricated by the manufacturer and then finished on site by the orthotist to meet the size and shape of the intended wearer. As can also be appreciated, the sleeves which are disposed between the inner and outer layers of soft compressible plastic material provide passageways into which the reinforcing stays can be easily inserted after the two layers have bonded to each other.

Various features and advantages will appear from the description to follow. In the description, reference is made to the accompanying drawings which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS:

In the drawings wherein like reference numerals represent like parts.

FIG. 3 is a perspective view partly broken away of an unfinished soft body brace constructed according to the teachings of the present invention for use in making the soft body brace shown in FIG. 1;

FIG. 7 is a perspective view of one of the sleeves in the unfinished soft body brace shown in FIG. 3;

FIG. 8 is a perspective view of one of the iliac crest pads in the unfinished soft body brace shown in FIG. 3 and;

FIG. 9 is a perspective view of one of the reinforcing stays in the unfinished soft body brace shown in FIG. 3.

DETAILED DESCRIPTION OF PREFERRED EMBODIMENTS

The present invention is directed to a soft body brace which provides an effective and tolerable means of spinal support for those patients who cannot tolerate rigid pressure point, non flexible compression or simply do not need rigid support and which can be customized on site to meet patient requirements.

Figure 1:
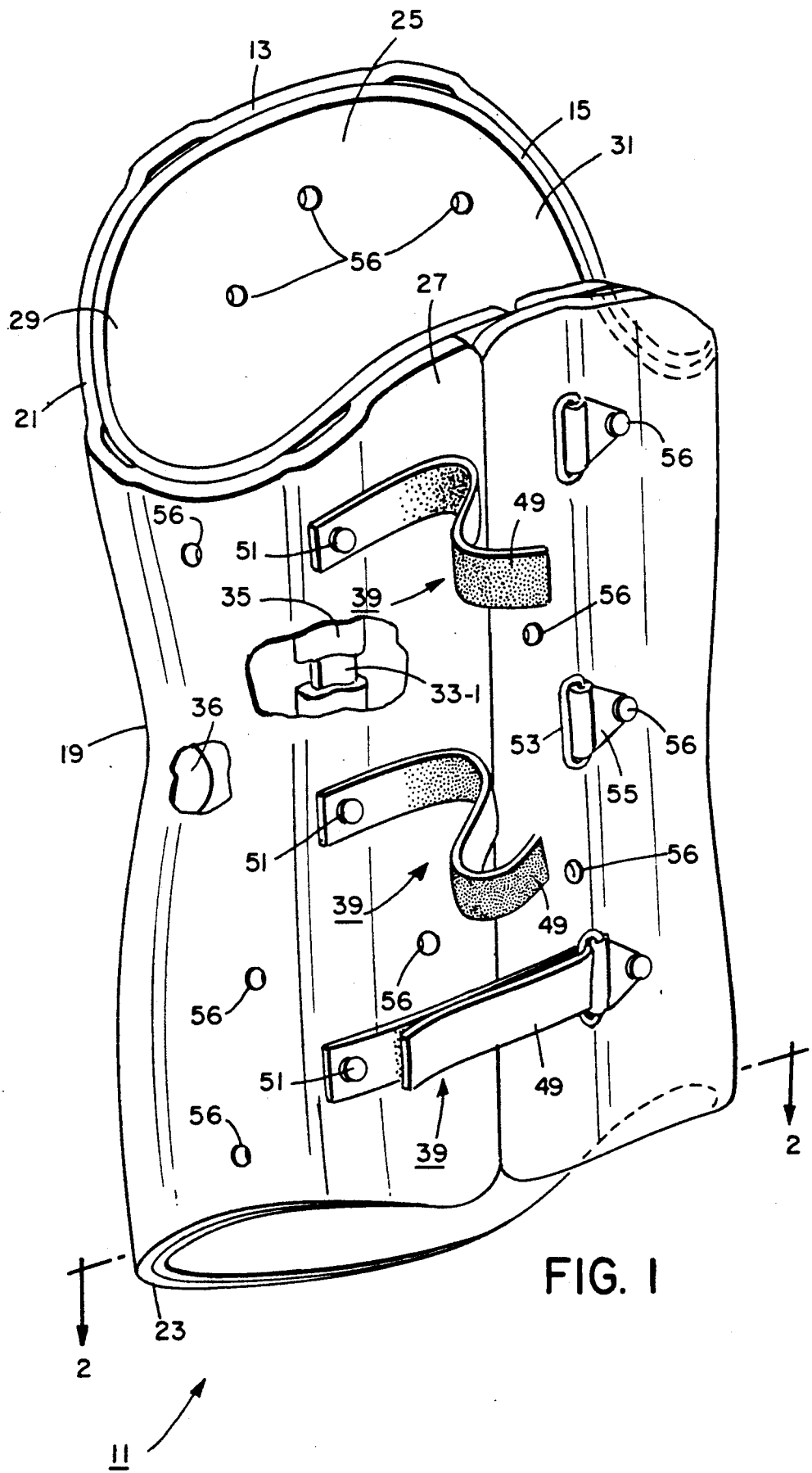
FIG. 1 is a perspective view partly broken away of a soft body brace constructed according to the teachings of the present invention.
Figure 2:
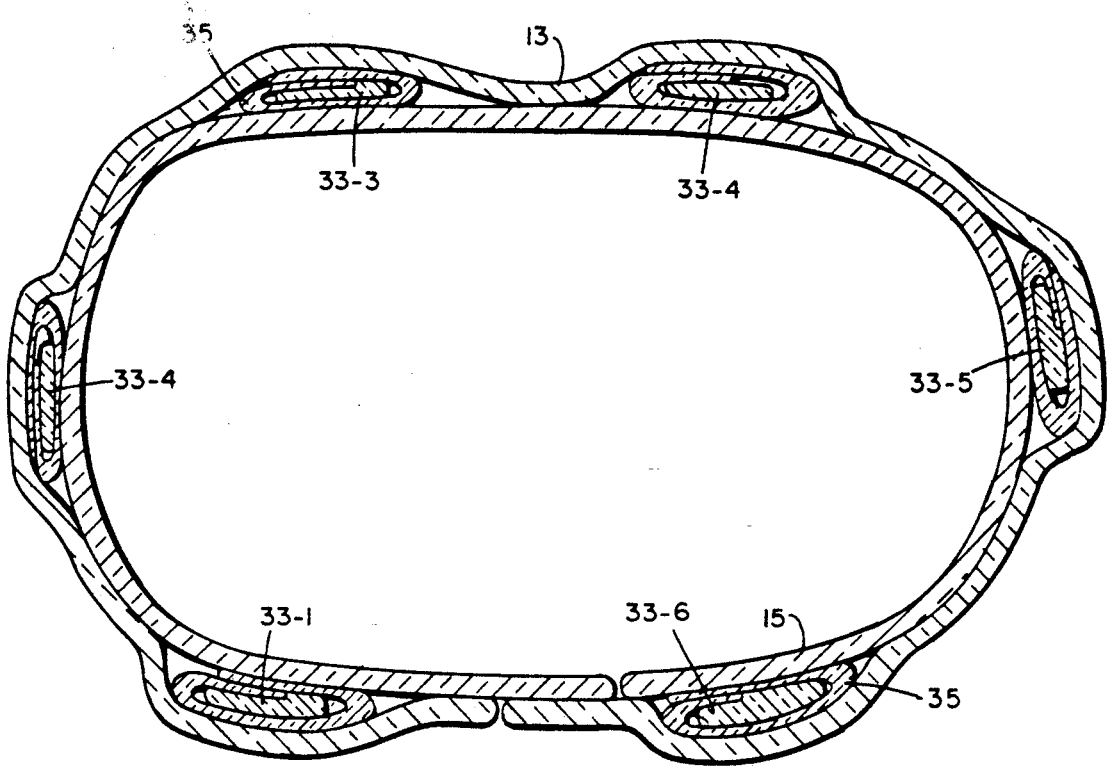
FIG. 2 is an enlarged cross section view taken along lines 2—2 in FIG. 1.

Referring now to the drawings, and first to FIGS. 1 and 2, there are shown perspective and cross-section views, respectively, of a soft body brace constructed according to the teachings of the present invention and identified generally by reference numeral 11.

Brace 11 is sized to circumscribe the torso and engage the pelvic area of a person on whom it is to be worn and comprises an outer layer 13 of soft compressible plastic material, such as polyethylene foam, and an inner layer 15 which is also of soft compressible plastic material, such as polyethylene foam. Layers 13 and 15 are each about ¼ of an inch thick. Inner layer 15 is bonded to outer layer 13. Outer layer 13 and inner layer 15 define a shell 19 having a top edge 21, a bottom edge 23, a posterior portion 25, a vertically split anterior portion 27 and side portions 29 and 31. Layer 13 is overlapping relative to layer 15 to prevent the body of the wearer from protruding from the split portion 27 when the brace is secured in place on the wearer.

Reinforcing stays 33-1 through 33-6 are provided to maintain shell 19 in its intended shape. Stays 33 are made of a plastic such as polyethylene and are about 5/32 of an inch thick. Alternately, stays 33 may be made of a metal such as aluminum. Stays are disposed in sleeves 35 which are fixedly sandwiched between layers 13 and 15. Sleeves 35 are made from a thin sheet of polyethylene, or other suitable material. The ends of sleeves 35 are closed so that stays 33 cannot fall out or be removed.

Iliac crest pads 36 for engaging the hips of the person when the brace is being worn are bonded in place between layers 13 and 15 behind sleeves 35. Pads 36 may be made of soft compressible plastic material such as polyethylene foam.

Releasable fastener assemblies 39 are fixedly attached to split anterior portion 27. Fastener assemblies 39 include VELCRO hook and loop type fastener straps 49 which are attached by rivets 51 to stay 33-1 on one side of the split anterior portion 27 and buckles 53 which are connected by chafes 55 to stay 33-6 on other side of the split anterior portion 27 by rivets 51.

Aeration holes 56 are provided throughout brace 11.

Body brace 11 is fabricated by first making an unfinished soft body brace and then trimming, shaping and finishing the unfinished soft body brace to meet the exact requirements of the person on whom it is to be worn. Advantageously, the unfinished soft body brace may be made by the manufacturer and then trimmed, shaped and finished on site by the orthotist.

Figure 5:
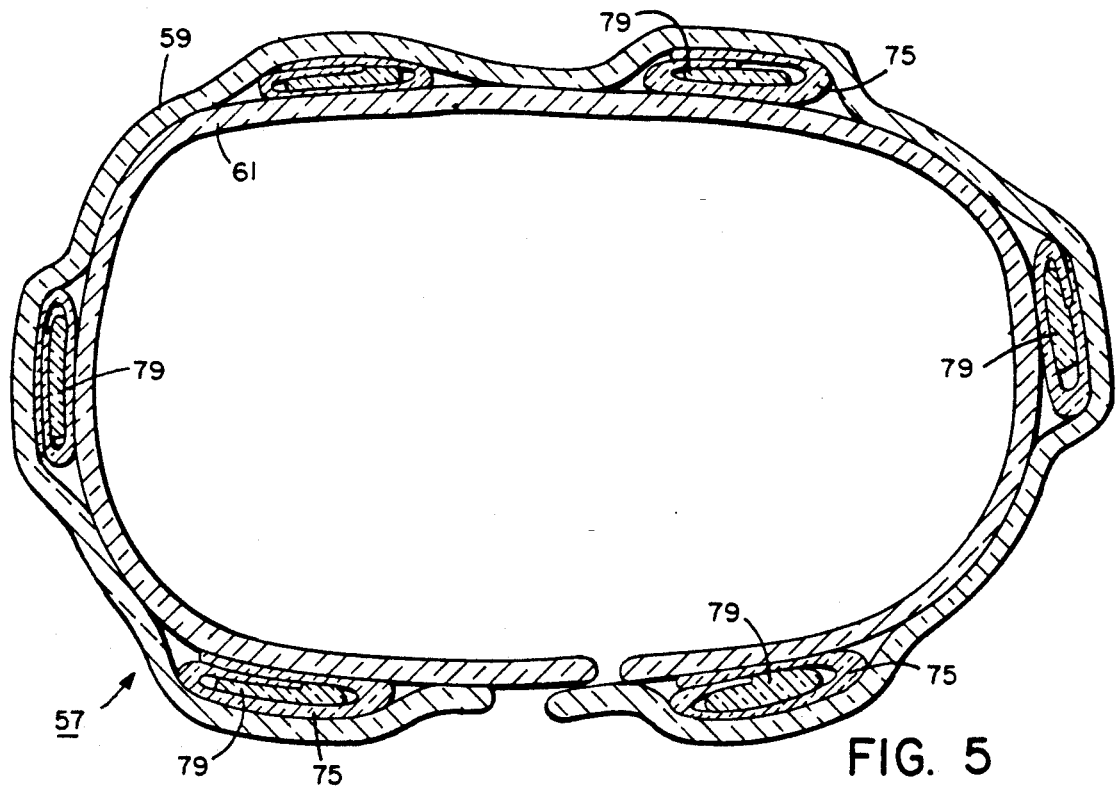
FIG. 5 is an enlarged cross-section view taken along lines 5—5 in FIG. 3.
Figure 4:
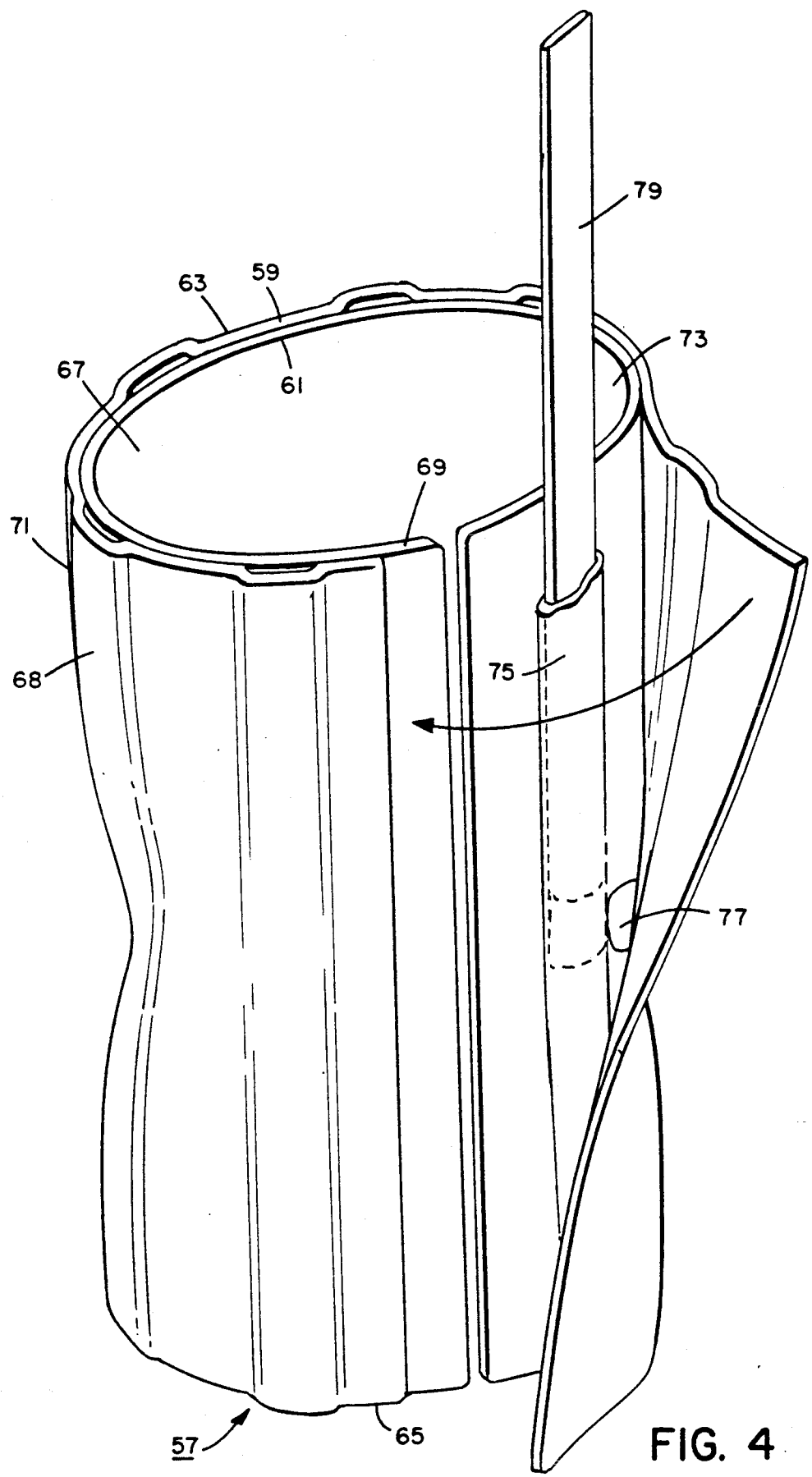
FIG. 4 is a perspective view of the unfinished soft body brace shown in FIG. 3 with the outer layer partially peeled away and with all but one of reinforcing stays removed.
Figure 6:
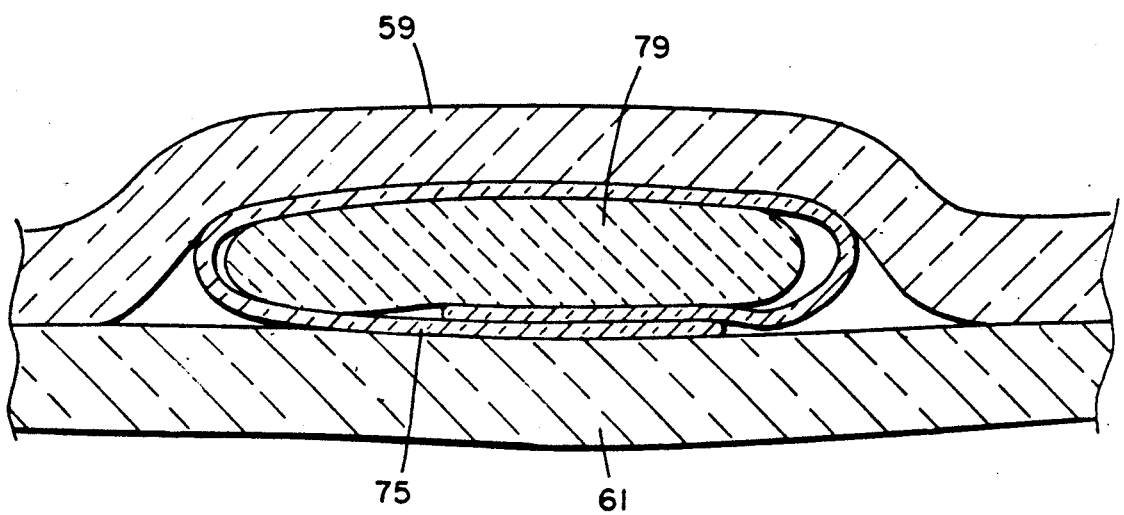
FIG. 6 is an enlarged fragmentary view of the cross-section shown in FIG. 5.

Referring now to FIG. 3 there is shown a perspective view partly broken away of an unfinished soft body brace constructed according to the teachings of the present invention and identified generally by reference numeral 57. A partly unravelled version of the brace with parts removed is shown in FIG. 4 and a cross-section view is shown in FIG. 5.

Unfinished soft body brace 57 is substantially cylindrically shaped structure comprising an outer layer 59 of soft compressible plastic material, such as polyethylene foam, about ¼ of an inch thick and an inner layer 61 which is also of soft compressible plastic material, such as polyethylene foam, also about ¼ of an inch thick. Inner layer 61 is bonded to outer layer 59. Outer layer 59 and inner layer 61 define a shell 62 having a top edge 63, a bottom edge 65, a posterior portion 67, a vertically split anterior portion 69 and side portions 71 and 73.

A plurality of elongated sleeves 75 are fixedly sandwiched between outer layer 59 and inner layer 61. Sleeves 75 are transversely spaced and vertically oriented. The length of sleeves 75 is at least equal to the distance from top edge 63 to bottom edge 65 of shell 62. Each sleeve 75 is made from a thin sheet of polyethylene or any other similar material. A perspective view of one of the sleeves is shown in FIG. 7. A pair of iliac crest pads 77 for engaging the hips of the wearer are bonded to inner layer 61 behind sleeves 75. Iliac crest pads 77 may be made of soft compressible plastic material such as polyethylene foam. One of the iliac crest pads 77 is shown in FIG. 8.

A reinforcing stay 79 about 5/32 of an inch thick and a cross section less than sleeve 75 and made of a plastic such as polyethylene or a metal such as aluminum is slidably and removably mounted in each sleeve 75. Stays 79 are preferably longer than brace 57 so that they can easily be inserted or withdrawn from sleeves 75. A perspective view of one of the reinforcing stays 79 is shown in FIG. 9.

Unfinished soft body brace 57 may be fabricated in the following manner. First, inner layer 61 is formed by heating a first sheet of soft compressible plastic material to a temperature such that it can be shaped as desired. The heated sheet is then wrapped around a plaster mold which is in the shape of the torso of a person and which is equipped with suction (i.e. vacuum means) so that the sheet can be sucked down to conform to its shape. Plaster molds equipped with suction and used for this purpose are well known and described, for example, in the above noted U.S. Pat. No. 3,871,367. While layer 61 is still hot, the iliac crest pads 77 are heated and then bonded to layer 61 at the proper locations. Then, sleeves 75 are heated and bonded in place on layer 61. Inserts (not shown) are preferably disposed in sleeves 75 when sleeves 75 are heated so that sleeves 75 will not close up on themselves. The inserts may comprise strips of polyethylene about 1/16 of an inch thick. Then, a plurality of small suction holes 79 are formed on layer 61 so that a second layer can be pulled over it. Then, a second sheet of soft compressible plastic material is heated. At the same time inner layer 61, while it is still on the mold, is heated again. The second sheet is then wrapped around inner layer 61, in overlapping relationship to form outer layer 59, sucked down by the vacuum to conform to the shape of the mold and allowed to cool.

At this stage, the unfinished body 57 so produced has not been customized to meet the specific shape and size requirements of the intended wearer and the fasteners have not been attached.

Unfinished soft body brace 57 may be made into a finished (i.e. customized) soft body brace as follows.

First, reinforcing stays 79 are removed and brace 57 trimmed to size. Then brace 57 is placed on the patient to determine areas which require reshaping. Brace 57 is then removed from the patient and heated up at those areas which must be modified, using a heat gun or other suitable means. While heated, brace 57 is placed again on the person on whom it is to be worn and then by finger pressure or other suitable means is shaped to conform to the shape of the person.

Then, brace 57 is allowed to cool.

Then, reinforcing stays 79 are cut as needed to the appropriate size, bent to conform to the shape of the patient at their intended locations and then inserted back into their respective sleeves 75. If stays 79 are made of polyethylene, they are heated first so that they can be bent to the desired contour.

After the stays have been inserted in the sleeves, the end of the sleeves are sealed off using heat or other means so that the stays cannot be removed.

The fasteners assemblies 47 are then attached to the brace.

The embodiments of the present invention is intended to be merely exemplary and those skilled in the art shall be able to make numerous variations and modifications to it without departing from the spirit of the present invention. For example, the iliac crest pads could be integrally formed with the inner layer of soft compressible plastic material. Also, stays could be positioned between the two layers at orientations other than vertical. Also the stays could be of shapes different than that shown (i.e. tapered or "U" shaped etc.) and the sleeves changed accordingly. The above and other such variations and modifications are intended to be without the scope of the present invention as defined in the appended claims.

What is claimed is:

1. An unfinished soft body brace for engaging the trunk of a person for supportive purposes comprising:

a. an inner layer of soft compressible plastic material, b. an outer layer of soft compressible plastic material bonded to the inner layer of soft compressible plastic material,
c. the inner and outer layers defining a shell having a split portion,
d. a plurality of flexible sleeves fixedly sandwiched between the outer and inner layers of soft compressible plastic material, and
e. reinforcing stays slidably and removably mounted in the sleeves.

2. The brace of claim 1 and wherein the stays are made of polyethylene.

3. The brace of claim 1 and wherein the stays are made of metal.

4. A finished soft body brace for engaging the trunk of a person for supportive purposes comprises:
a. an outer layer of soft compressible plastic material,
b. an inner layer of soft compressible plastic material bonded to the outer layer of soft compressible plastic material,
c. the inner and outer layers defining a shell having a split portion, said shell having a shape conforming to the shape of a person on whom the brace is to be worn,
d. a plurality of flexible sleeves fixedly sandwiched between the outer and inner layers of soft compressible material,
e. a reinforcing stay fixedly disposed in each sleeve, and
f. releasable fastener means secured to the split portion of the shell.

5. The brace of claim 4 and further including iliac crest pads disposed between the inner and outer layers.

6. The brace of claim 4 and wherein the iliac crest pads are made of polyethylene.

7. The brace of claim 4 and wherein the reinforcing stays are made of plastic.

8. The brace of claim 4 and wherein the reinforcing stays are made of polyethylene.

9. The brace of claim 4 and wherein the stays are transversely spaced and vertically oriented.

10. The brace of claim 4 and wherein the inner and outer layers are made of polyethylene foam.

11. The brace of claim 4 and wherein the sleeves are made of polyethylene.

12. The brace of claim 4 and wherein the stays are made of metal.

13. An unfinished soft body brace for engaging the trunk of a person for supportive purposes comprising:
a. an inner layer of soft compressible plastic material,
b. an outer layer of soft compressible plastic material bonded to the inner layer of soft compressible plastic material,
c. the inner and outer layers defining a shell having a split portion,
d. a flexible sleeve fixedly sandwiched between the outer and inner layers of soft compressible plastic material, and
e. a reinforcing stay slidably and removably mounted in the sleeve.

* * * * *